United States Patent [19]

Hufenreuter

[11] 4,208,127

[45] Jun. 17, 1980

[54] CUVETTE HOLDER

[75] Inventor: Wolfgang Hufenreuter, Müllheim, Fed. Rep. of Germany

[73] Assignee: Helma GmbH & Co. KG, Müllheim, Fed. Rep. of Germany

[21] Appl. No.: 878,744

[22] Filed: Feb. 17, 1978

[30] Foreign Application Priority Data

Feb. 19, 1977 [DE] Fed. Rep. of Germany ....... 2707231

[51] Int. Cl.² ............................................. G01N 21/00
[52] U.S. Cl. .................................................. 356/244
[58] Field of Search ........................................ 356/244

[56] References Cited

U.S. PATENT DOCUMENTS 3,927,794  8/1976  Liedholz .............................. 356/244
4,047,820  9/1977  Soodak et al. ....................... 356/244

FOREIGN PATENT DOCUMENTS 1287820  1/1969  Fed. Rep. of Germany ........... 356/244

*Primary Examiner*—John K. Corbin
*Assistant Examiner*—Matthew W. Koren
*Attorney, Agent, or Firm*—Michael J. Striker

[57] ABSTRACT

A holder for polygonal cross-section cuvettes is provided. The holder comprises a handle having and lying on an axis, and a holding plate connected to and extending radially from the handle. The holding plate is formed with a plurality of apertures each having a periphery. The periphery is formed with a plurality of notches corresponding in number and arrangement to the longitudinally directed edges of a polygonal-section cuvette. Inwardly concave portions are formed between the notches and connect the same in such a manner that a cuvette inserted in an aperture is held only at its longitudinally directed edges which engage only the notches. A supporting plate is also provided. This support plate is connected to the handle and spaced from and generally parallel to the holding plate in such a manner that a cuvette inserted in an aperture stands on the support plate.

10 Claims, 2 Drawing Figures

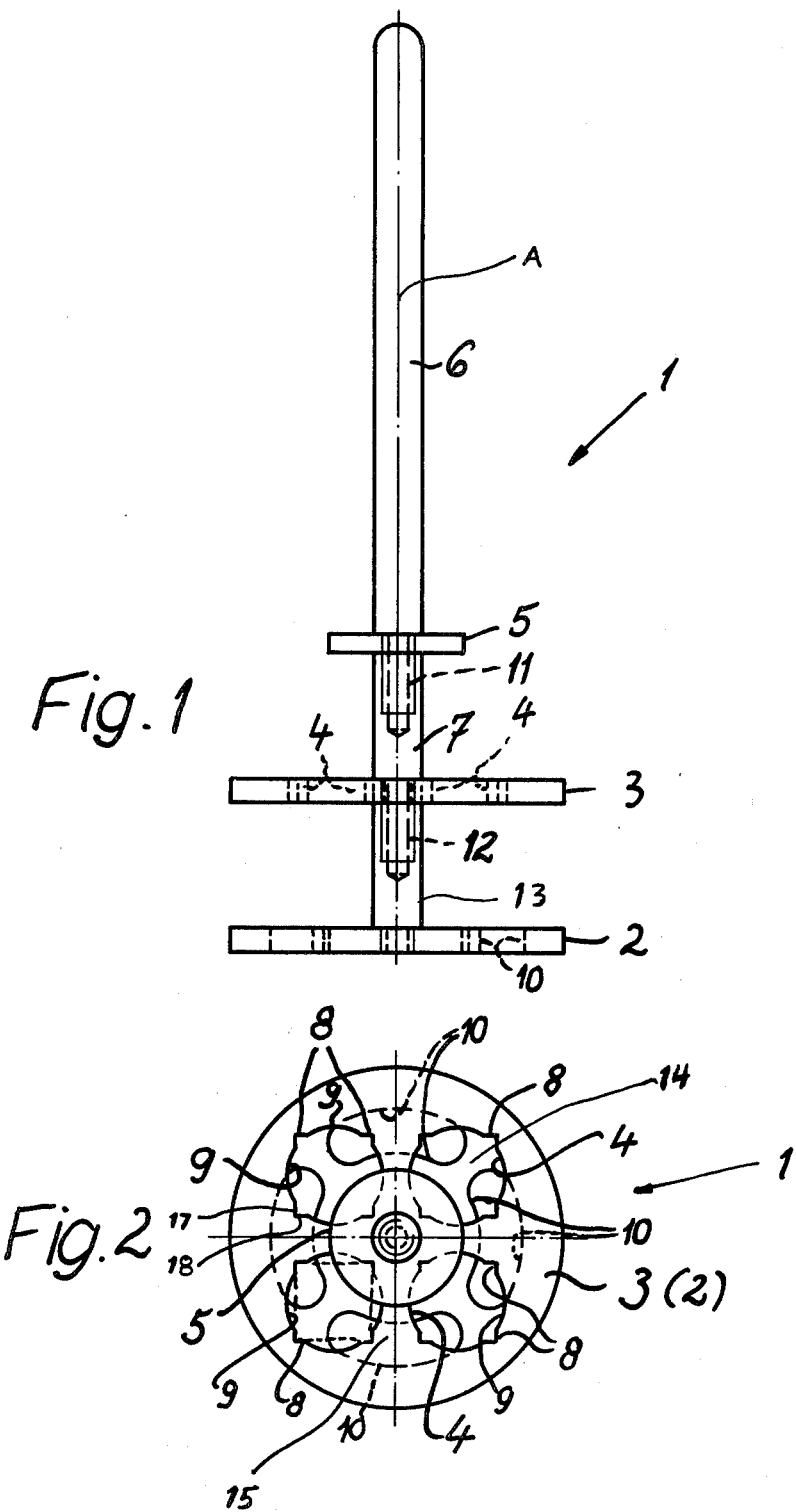

CUVETTE HOLDER

BACKGROUND OF THE INVENTION

The invention relates to a cuvette holder. A cuvette is an at least predominantly transparent container which holds a liquid while e.g. its optical properties are measured. Typically, cuvette holders include a holding plate with apertures for embracing a cuvette, and a supporting plate connected to but spaced below the holding plate and upon which the bottom of the cuvette rests. Advantageously, the cuvette holders are also provided with both a detachable retaining flange or the like which covers the top of the cuvette and which has a center which is connected to the center of the holding plate, and a handle connected to and projecting upwardly from the center of the supporting flange.

The apertures of the holding plate have a size corresponding to the cross section of the cuvette. What the conventional art has not solved is the problem of how to keep the apertures clean. When a cuvette is contaminated, some of the contaminant may stick in a moistened aperture; then, the contaminant may be transferred to the next cuvette inserted in the aperture for cleaning. This problem is of particular significance for cuvettes when the contaminants may be transferred to the area of the window surfaces of the cuvette. Light passing through contaminated window surfaces may be absorbed or deflected so as to give an inaccurate reading of the optical properties of the liquid inside the cuvette.

SUMMARY OF THE INVENTION

The main object of the invention is to provide a cuvette holder which is designed in such a manner that it does not pass contaminants from one cuvette to the window surfaces of another.

Another object of the invention is to simultaneously provide a cuvette holder which can be used in a conventional cuvette cleaning apparatus.

In accordance with the inventive concept, the shape of the apertures of the holding plate is altered. Each aperture is formed with a plurality of notches corresponding in both number and arrangement to the longitudinally extending edges of a polygonal-section cuvette. Inwardly concave portions connect the notches in such a manner that a cuvette is confined within said apertures but is held only at its corners where it is engaged by the respective notches. The benefit of this inventive reshaping of the apertures is that the side faces or windows of each cuvette are kept substantially free of contact with peripheral portions of the apertures of the cuvette holder, these side faces will not be contaminated with any impurities adhering to the peripheral portions of the apertures. To hold cubic cuvettes, the apertures have four notches, arranged as two pair of notches located opposite each other. Each notch lies in a plane of another notch and is spaced from the other notches in such a manner that the four longitudinally directed edges of the cube fit into the four notches.

Preferably the inwardly concave connecting portions are shaped as circular arc sections for purposes of easy construction.

The supporting plate may have apertures which lie below the apertures of the holding plate. The apertures of the supporting plate may be uniform in both shape and size. The apertures of the supporting plate are provided for the purpose of avoiding obstruction of sonic waves directed toward the bottom end of the cuvette or to rapidly drain a cleaning liquid as the cuvette holder is taken out of a cleaning bath. The shape of the apertures of the supporting plate must be such that the cuvette will not fall through. Relative to the orientation of the handle, each of these apertures is advantageously radially smaller than any one of the apertures of the holding plate. In such a case, the apertures of the supporting plate may be longer in the circumferential direction of the plate than the apertures of the holding plate.

When the supporting plate has oblong apertures of the foregoing description, a cleaning jet from below may be directed against and inside a cuvette which is inserted in the holding plate in such a manner that its open side is facing downwardly against the supporting plate. Alternatively, when the closed bottom side of the cuvette is facing against the supporting plate, such a cuvette holder may be used in an ultrasonic cleaner since the apertures of the holding plate permit maximum access of the sonic waves to the interior of the cuvettes.

A particularly advantageous relationship between the apertures of both plates comes about when each plate has an equal number of apertures and, on the supporting plate, each separating portion which separates two adjacent apertures is aligned substantially below the center of a respective one of the holding plates. Each aperture of the supporting plate is aligned so that its circumferential length is aligned below adjacent portions of two of the apertures of the holding plate. On the holding plate, each separating portion separating two adjacent apertures is then in a position over approximately the center of a respective one of the supporting plate apertures. With maintenance of this relationship, the side faces of each of the cuvettes are subjected to an improved cleaning action since the cuvette is exposed to jets of cleaning liquid or to sonic waves passing through two supporting plate apertures.

The cuvette holder may also be provided with a retaining flange extending radially from the handle and with a thread extending axially therebelow. The retaining flange serves to cover the cuvettes, and the thread serves to fasten the handle and flange to a coupling rod connecting the plates. The coupling rod may be formed of two sections, one of which also has a threaded portion and the other of which receives it. The first section may extend axially above the holding plate and include a portion reciprocally shaped relative to the thread of the handle. The first portion may also have a threaded portion extending axially below the holding plate. The second section may project axially above the supporting plate and have a reciprocally shaped portion for fitting the threaded portion of the first section therein. When assembling the inventive cuvette holder, the first section is screwed to the second section and the handle is screwed to the first section. The threaded connections provide a particularly firm fit which assures a reliable fastening of the components of the cuvette holder.

The inventive cuvette holder may consist at least partially if not totally of synthetic resin.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a side view of an embodiment of the inventive cuvette holder; and

FIG. 2 is a perspective view of the same embodiment showing preferred shapings of the apertures of the holding plate and the supporting plate.

DESCRIPTION OF A PREFERRED EMBODIMENT

As shown by FIG. 1, the cuvette holder is provided at its bottom with a supporting plate 2. A holding plate 3 is parallel to and upwardly spaced from the supporting plate 2 and includes a plurality of apertures 4 each of which can embrace a cuvette. A cuvette embraced by a respective one of apertures 4 will stand on supporting plate 2, and the top of the cuvette will upwardly extend beyond the respective aperture 4.

A retaining flange 5 is provided at the lower end of a handle 6. The handle 6 is detachably connected at its lower end to the centers of the plates 2 and 3. The retaining flange then covers the top portions of the cuvettes so that they do not fall out of their respective apertures 4. As shown in FIG. 1, a coupling rod 7 extends upwardly from holding plate 3. The handle 6 is directly detachably connected to coupling rod 7, and then has end which lies on an axis A. Plates 2 and 3 extend radially from this axis A.

As shown by FIG. 2, the apertures 4 of the holding plate 3 are each formed with a plurality of notches 8 corresponding in both number and arrangement to the longitudinally extending edges of a polygonal-section cuvette. To hold a cubic cuvette, each aperature is provided with four notches 8 which are arranged as two pair of notches 8, each notch 8 of the pair being located opposite the other. Each notch lies in a plane which includes another notch and is spaced from this other notch 8 in such a manner that a longitudinally extending side of the cuvette passes therebetween and the longitudinally extending edges of the cuvette each engage a respective one of the notches 8.

Where the apertures 4 are also formed by circular arc sections 9 connecting the notches 8, as shown in FIG. 2, the notches 8 are arranged in pairs, each notch 8 of the pair being located radially opposite the other notch 8 of the pair.

Preferably the circular arc sections 9 are of a uniform size and together define portions of the radius of curvature having a common midpoint in the center of the respective aperture 4 so that the circular periphery is defined by four circular arc portions each being spaced about 90° from each other by two of the four notches 8. Each of the longitudinally extending edges of a cubic cuvette can be inserted in a respective one of the notches 8. By virtue of the inwardly concave nature of the circular arc sections, the side faces of the cuvette are spaced from and do not touch these arc sections, at least to any significant extent. Therefore, contaminants adhering to these arc sections will not be transferred to the side faces of the cuvette so as to thereby falsify an optical reading. The notches 8 are not of sufficiently great size to contact and thereby possibly contaminate any significant portion of the side faces.

Also in accordance with the inventive concept, the supporting plate 2 is provided with apertures 10. Apertures 10 in the preferred embodiment are uniform in both shape and size. However, the apertures 10 are shaped in such a manner that the cuvettes will not fall therethrough. Apertures 10 are completely defined by supporting plate 2 and are circumferentially spaced from each other. Relative to the axis A, each aperture 10 is radially smaller than any one of the respective apertures 4, but is longer in the circumferential direction of the plate than any one of the respective apertures 4. These apertures 10 provide access for a cleaning means through the bottom of the supporting plate 2. This is particularly important for cleaning baths and for ultrasonic cleaners. The inventive cuvette holder can then have a double function on the one hand, it can be used during the measurement of the optical properties of a liquid within the cuvettes, and on the other hand it can be used during the cleaning of these cuvettes by inserting it into a selected cleaning apparatus. For washing, the cuvettes can simply be inverted so that their open end faces the supporting plate 2 so that the cleaning means can enter the cuvette through the apertures 10.

The apertures 10 are oblong holes passing through the supporting plate 2, each aperture being spaced from two neighboring apertures by a separating portion 14 of the plate 2. The apertures 4 are correspondingly spaced by separating portion 15 of plate 3. If suitable, apertures 4 and 10 can be superposed. In the preferred embodiment, apertures 4 and 10 are arranged in such a manner that each separating portion 14 lies straight under the center of a respective aperture 4, and each separating portion 15 lies straight over the center of a respective aperture 10. In this embodiment, the apertures 10 are sufficiently elongated (or "oblongated") to such an extent that two ends of two different oblong apertures 10 are aligned with the aperture 4. This embodiment is useful when cleansing action by upwardly directed jets of cleaning liquid is contemplated, since the spatial orientation of the apertures 10 relative to the cuvettes held in apertures 4 permits an optimum access to the interior of the cuvette while still adequately supporting the cuvette.

Extending radially below the lower end of the handle 6 and the retaining flange 5 is a thread 11 which is detachably connected with the coupling rod 7 to the plates 2 and 3. The coupling rod 7 may have two sections; a first section 7 extending above plate 3 and having an axially downwardly extending threaded portion 12, and a second section 13 extending above plate 3 and having a hollow portion reciprocally shaped relative to the threaded portion 12, this hollow portion engaging the threaded portion 12. This form of attachment of the components of the inventive cuvette holder provides for easy detachment by simply unscrewing the components. Also, the cuvette holder can be adapted to differently sized cuvettes by simply substituting a component with a differently sized thread.

A particularly simple mode of production can be achieved when at least part of the individual components of the inventive cuvette holder are made of synthetic resin.

Preferably, the notches 8 are formed by two straight cuts 18, 17 each less than one millimeter in length so that a longitudinally extending edge of a cuvette is pressed against the two cuts 18, 17 of the notch with the notch being completely free of contact with the side window faces of the cuvette. With notches of such a size, the window faces are not susceptible to be smudged by residual contaminants which might adhere to the noches. The inventive cuvette holder can also be used for the preparation of the cuvettes for the optical measurements. If a drop of the liquid to be measured happens to run down the side of a cuvette and then wets the holding plate portions defining aperture 4, the side faces of the next cuvette inserted into the aperture 4 will not be moistened because of their spacing between these faces and the inwardly concave, preferably circular arc section.

It will be understood that each of the elements described above, or two or more together, may also find a useful application in other types of a cuvette holder differing from the types described above.

While the invention has been illustrated and described as embodied in a holder, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A holder for cleaning, drying and storing of polygonal cross-section cuvettes, said holder comprising in combination a supporting plate having an axis and arranged so that a cuvette stands by its bottom end on said support plate; a plate-shaped retaining flange axially spaced from and located generally parallel to said supporting plate, so that the cuvette standing on said supporting plate is engaged at its top end by said retaining flange, said retaining flange being provided with a handle coaxial to and connected with said supporting plate; and a holding plate located axially between and parallel to said supporting plate and said retaining flange and connected with said handle, said holding plate being formed with a plurality of apertures each having a periphery formed with a plurality of notches corresponding in number and arrangement to the longitudinally directed edges of a polygonal cross-section cuvette and formed between said notches with inwardly concave connecting portions, whereby a cuvette inserted in one of said apertures so as to stand on said supporting plate and to be retained by said retaining flange is unobstructed both in the region between said supporting plate and said retaining flange and within said holding plate in the regions of said inwardly concave connecting portions of said apertures so as to prevent contamination of and allow sufficient access of cleaning means to the cuvette.

2. The holder of claim 1, said apertures of said holding plate being circumferentially spaced from each other.

3. The holder of claim 1, each notch being formed by two straight cuts each being less than one millimeter in length.

4. The holder of claim 1, each notch being right-angled.

5. The holder of claim 1, each notch lying in a plane of another notch.

6. The holder of claim 1, said connecting portions being uniformly sized, each connecting portion being a circular arc section and being spaced from each other by such a distance that each connecting portion is spaced from a respective one of the longitudinally extending window faces of a cuvette inserted in one of said apertures of said holding plate, and said notches being arranged in pairs, the notches of each pair being radially opposite each other.

7. The holder of claim 1, said supporting plate also being formed with a plurality of apertures lying below said apertures of said holding plate, each aperture of said supporting plate having a dimension extending radially relative to said axis, said dimension being smaller than the width of a cuvette, whereby a cuvette is supported by portions defining each aperture of said supporting plate while a cleaning medium has access to the cuvette from areas below said supporting plate.

8. The holder in claim 7, said apertures of said supporting plate corresponding in number to said apertures of said holding plate, said apertures of said supporting plate being oblong, each aperture of said supporting plate having a circumferential length longer than that of any of said apertures of said holding plate, whereby access of a cleaning medium to said cuvette from below said supporting plate is improved.

9. The holder of claim 8, said supporting plate including a plurality of first separating portions corresponding in number to said apertures of said supporting plate and separating the same from each other, said holding plate including a plurality of second separating portions corresponding in number to said apertures of said holding plate and separating the same from each other, said holding plate and said supporting plate being arranged relative to each other in such a manner that each first separating portion is located below the center of a respective one of said apertures of said holding plate, each second portion is located above the center of a respective one of said apertures of said supporting plate, and each aperture of said holding plate is superposed over portions of two apertures of said supporting plate, whereby optimum cleaning of each cuvette can be achieved while supporting each cuvette on said supporting plate.

10. The holder of claim 1, said handle including a threaded portion axially below said retaining flange, said threaded portion being detachably connected to said holding plate; said holding plate being formed with apertures which are circumferentially spaced from each other and which are formed with four right-angled notches each lying in a plane of another notch and with four circular arc section connecting portions which connect the notches, said circular arc connecting portions being radially spaced from each other by a distance greater than the width of a cuvette; and said supporting plate also being formed with a plurality of apertures lying below said apertures of said holding plate, each aperture of said supporting plate having a radially extending dimension which is smaller than the width of a cuvette wherein at least part of the cuvette holder is made of plastic.

* * * * *